United States Patent

Hach

[11] 4,025,309
[45] May 24, 1977

[54] CARBON NITROGEN TEST SYSTEM

[75] Inventor: Clifford C. Hach, Ames, Iowa

[73] Assignee: Hach Chemical Company, Ames, Iowa

[22] Filed: Feb. 26, 1976

[21] Appl. No.: 661,741

[52] U.S. Cl. .................. 23/230 PC; 23/253 PC
[51] Int. Cl.² .................. G01N 7/08; G01N 25/24; G01N 31/10; G01N 31/12
[58] Field of Search ...... 23/230 PC, 253 PC, 254 E

[56] References Cited

UNITED STATES PATENTS

| 2,991,684 | 7/1961 | Wever | 23/230 PC X |
| 3,062,624 | 11/1962 | Peifer | 23/230 PC UX |
| 3,226,197 | 12/1965 | Lewis | 23/253 PC X |
| 3,647,387 | 3/1972 | Benson et al. | 23/230 PC |
| 3,652,227 | 3/1972 | Harman et al. | 23/232R |
| 3,838,969 | 10/1974 | Dugan | 23/253 PC X |

OTHER PUBLICATIONS

Fontyn et al., Homogeneous Chemiluminescent Measurement of Nitric Oxide with Ozone, Analyt. Chem. vol. 42, No. 65/70.

*Primary Examiner*—Morris O. Wolk
*Assistant Examiner*—Michael S. Marcus
*Attorney, Agent, or Firm*—Leydig, Voit, Osann, Mayer & Holt, Ltd.

[57] ABSTRACT

An analytical method for determining the elemental carbon and nitrogen contents of a sample. The sample, as a liquid or in finely divided solid form is placed in an evacuable pressure vessel and is then oxidized with a cupric oxide oxidizing agent to convert carbon to $CO_2$, nitrogen to $N_2$, and hydrogen to water. After cooling to condense the water, the resulting pressure provides a measure of the total carbon plus nitrogen content of the original sample. An aliquot of the gas is then treated for $CO_2$ removal, and the resulting change in volume thereby provides a measure of the ratio of carbon to nitrogen in the original sample.

4 Claims, 3 Drawing Figures

CARBON NITROGEN TEST SYSTEM

This invention relates to the determination of the carbon and nitrogen contents of a sample, and more particularly provides an analytical technique for determining the elemental carbon and nitrogen contents of a combustible sample.

Many techniques are known for accurately determining the elemental carbon and nitrogen contents of oxidizable samples. These techniques generally involve the controlled oxidation of a sample whereby carbon is converted to $CO_2$, nitrogen to $N_2$, and hydrogen to water followed by the careful collection and analysis of the resulting gas.

While employed widely, these techniques suffer many disadvantages which have heretofore limited their applicability to well-equipped laboratories and have restricted their use in the field. From the standpoint of a farmer who wishes to determine the organic nitrogen (i.e., protein) content of animal feeds with a view toward providing feed supplements, delays in transporting samples to an analytical laboratory and awaiting receipt of the analysis are intolerable. Accordingly, an object of the invention is to provide an analytical system for determining the elemental carbon and nitrogen contents of a sample, which system is suitable for portable, on-site use.

Another disadvantage of many of these existing analytical techniques is that they require sources of pure gases, e.g., oxygen and carbon dioxide, and require the preparation and standardization of analytical reagents, together with tedious titrations. Another object is to provide such technique which requires no extraneous gases, no analytical grade reagents, no standardization, and no titration procedure.

Still another detriment to the more widespread availability of analytical methods for determining carbon and nitrogen contents is the requirement of many of them that delicate mechanical or electronic laboratory equipment be employed. Still another object of the invention is to provide an analytical method which requires only one accurate weighing, and no sophisticated measuring beyond those commonly and routinely employed by industrial or agricultural technicians.

An overall object is to provide a method and portable apparatus for determining the elemental carbon and nitrogen contents of combustible samples, which is low in equipment cost, low in operating cost, employs only rugged instrumentation, and is suitable for rapid, accurate measurements of total carbon and total nitrogen contents.

The invention will be more fully described in conjunction with the attached drawings, wherein.

In accordance with the invention, an analytical method and apparatus are provided for determining the elemental carbon and nitrogen contents of a sample, particularly a combustible organic sample by an improved combustion and measurement technique. Typical of such samples may be cattle feed, grains for animal or human consumption, or various feeds and products in fermentation processes. Also the amount of organic matter can be determined in such materials as argicultural soil, or in oil shale.

Figure 1:
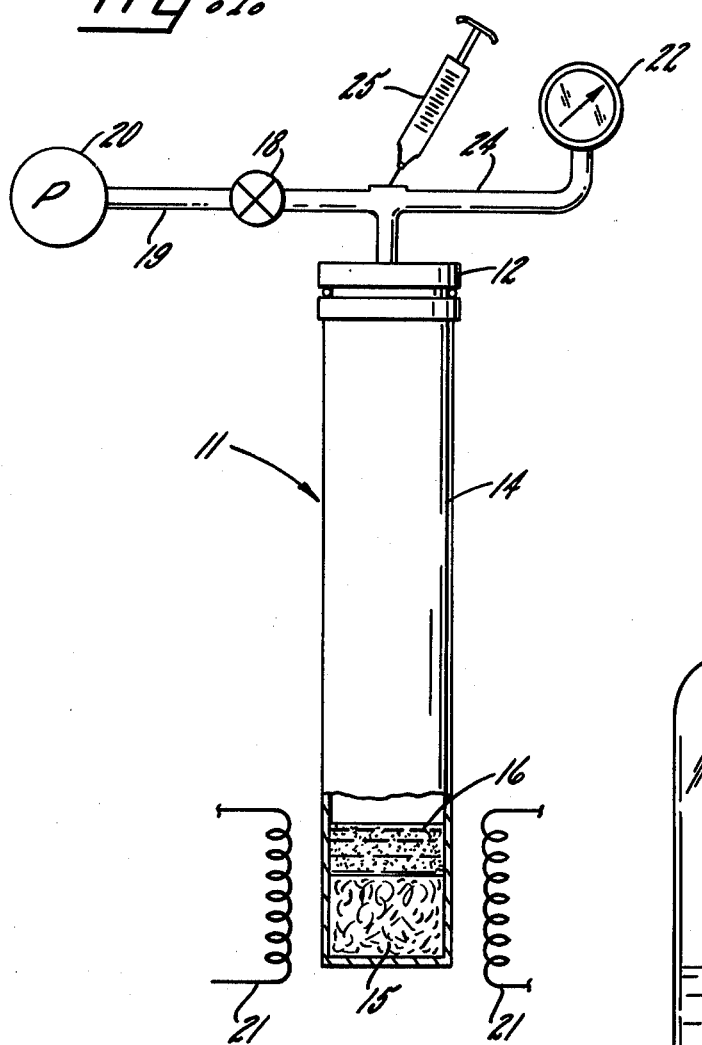
FIG. 1 is a schematic of an apparatus suitable for conducting the controlled oxidation of a sample in accordance with the invention.

In further keeping with the invention, and inviting attention to FIG. 1, an evacuable pressure vessel 11 is provided with a pressure-type closure 12 and a sample-receiving elongated body portion 14.

Into the bottom of vessel 11 is placed an accurately weighed liquid or finely divided solid combustible organic sample 15, which has been intimately admixed with a powdery or granular cupric oxide oxidizing agent. The agent is advantageously employed in substantial excess over that stoichiometrically required for combustion of the sample 15; that is, for conversion of all of the combined carbon to carbon dioxide ($CO_2$), all of the organic (and inorganic) nitrogen to nitrogen gas ($N_2$), and all of the hydrogen to water. Any additional elements, such as sulfur, phosphorous, or trace heavy metals, are similarly oxidized to their respective oxides, while the cupric oxide is reduced to elemental copper.

Atop the sample 15 is advantageously placed a secondary combustion layer 16 composed of an additional cupric oxide oxidizing agent. This is for the purpose of assuring, so far as possible, complete combustion of the carbon to the dioxide and of volatile carbonaceous co-products to the desired $CO_2$, $N_2$ and water.

After placing the sample 15 and the superimposed cupric oxide layer 16 into the vessel 11, the vessel is evacuated via a valve 18 equipped conduit 19 leading to a vacuum pump 20. The degree of vacuum is not critical, but for maximum precision in the subsequent determination of the ratio of carbon to nitrogen, it is desired that as much as possible of the ambient atmosphere be removed before the sample 15 is oxidized. Otherwise, excess oxygen or nitrogen from the atmosphere would create an error in the subsequent carbon/nitrogen ratio determination.

Once the vessel 11 is evacuated, the valve 18 is closed off and the bottom sample-containing portion of the vessel 11 is heated, advantageously with an external electrical heater 21, to a temperature sufficiently high to effect essentially complete oxidation of the sample 15 to $CO_2$, $N_2$ and water. A temperature of about 650° C and a time of approximately 5–10 minutes has been found to be adequate for complete combustion. Suitable thermocouples and/or timers may be employed to control the combustion temperature and/or time, but these are omitted from the drawing for reasons of clarity.

After combustion has been completed, the vessel 14 is then cooled to a temperature sufficiently low to condense most of the water of combustion. A water bath is convenient for this purpose, although any temperature approximating that of room temperature or below is sufficient to condense out enough water such that the vapor pressure does not significantly interfere with the experimental accuracy of the present system.

With water of combustion having been removed by condensation, the next step is merely to read the absolute pressure on a Burdon tube pressure gauge 22, connected by an open line 24 to the pressure vessel 11. This pressure, it will be appreciated, results from carbon dioxide plus nitrogen, and thus is proportioned to the total carbon plus nitrogen content of the original sample.

To compute the total carbon plus nitrogen content of the sample, it is only necessary to know the initial sample 15 weight, the volume of the vessel 11 along with the associated tubing 24 and the pressure gauge 22, and the absolute pressure recorded by the gauge 22. For approximate calculations the temperature may be assumed to be constant at about room temperature, e.g., 16° C, as this only introduces a minor error in the computations. Then, by conventional reference to the gas laws, the total number of moles (or millimoles) of carbon (from $CO_2$) plus nitrogen (calculated as $N_2$) may then be calculated, and this related to the initial quantity of both in the original sample 15. Alternatively, a chart may be prepared for any given initial quantity of the sample 15, in which event sample preparation entails the accurate determination of the quantity of sample corresponding to the particular chart being employed.

Figure 2:
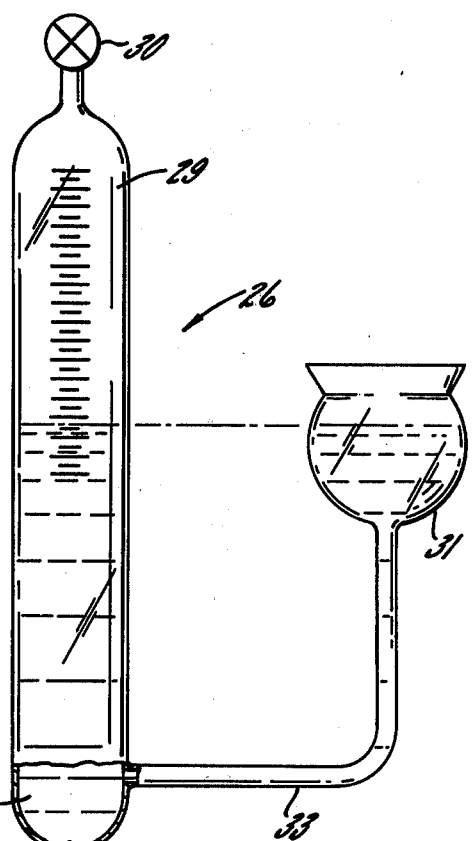
FIG. 2 is a schematic of a device in accordance with the invention for sorbing carbon dioxide from a sample aliquot containing nitrogen and carbon dioxide.

After having determined the resulting gas pressure in the vessel 11 and associated auxiliaries as a measure of the total carbon plus nitrogen content of the original sample, a predetermined volume of the gas is withdrawn for subsequent analysis and determination of the ratio of carbon to nitrogen in the original sample. To this end, a gas hypodermic syringe of, for example, 50 cc. volume, is employed to withdraw an aliquot sample of gas from the vessel 11 and to transfer the gas to a nitrometer apparatus 26, as shown in FIG. 2. The syringe 25 conveniently is inserted into the vessel 11 (FIG. 1) via a rubber cap (not shown) or directly through the walls of the rubber tube or conduit 24 so as to withdraw the gas, and is similarly inserted through a rubber cap 28 (FIG. 2) into the nitrometer apparatus 26.

As is conventional, the nitrometer apparatus 26 includes a volume-calibrated upper section 29 equipped with a vent valve 30, and a pressure equalizing flask 31 connected via a flexible conduit 33 near the bottom portion of the nitrometer apparatus 26.

To sorb carbon dioxide selectively from the mixture of nitrogen and carbon dioxide introduced via the syringe 25, the nitrometer apparatus 26 contains an alkaline liquid 32, e.g., aqueous potassium or sodium hydroxide, which is capable of reacting with the acidic $CO_2$ and thereby sorbing the same.

Operation of the nitrometer device is conventional. The predetermined aliquot of gas, at atmospheric pressure, is introduced from the syringe 25 into the apparatus 26 via the rubber cap 28, whereupon the gas bubbles upward through the liquid 32. The acidic $CO_2$ (and any other acidic gases that may be present in lesser amount, e.g., $SO_2$) reacts with the alkaline liquid 32 and is thus absorbed. Manual adjustment of the flask 31 so that the top level of the liquid in this flask corresponds with the meniscus of the liquid 32 in the apparatus 26 equalizes the gas pressure of the upper portion 29 of the apparatus, enabling the volume of non-absorbed gas (i.e., presumed to be $N_2$) to be measured. By measuring the volumetric ratio of non-absorbed gas ($N_2$) to the initial volume of the syringe 25 (50 cc's), the ratio of atoms of carbon to atoms of nitrogen in the original sample may be computed. Knowing the total atoms of carbon plus nitrogen, and the ratio of carbon to nitrogen, the elemental carbon and nitrogen contents of the original sample are readily determined.

Figure 3:
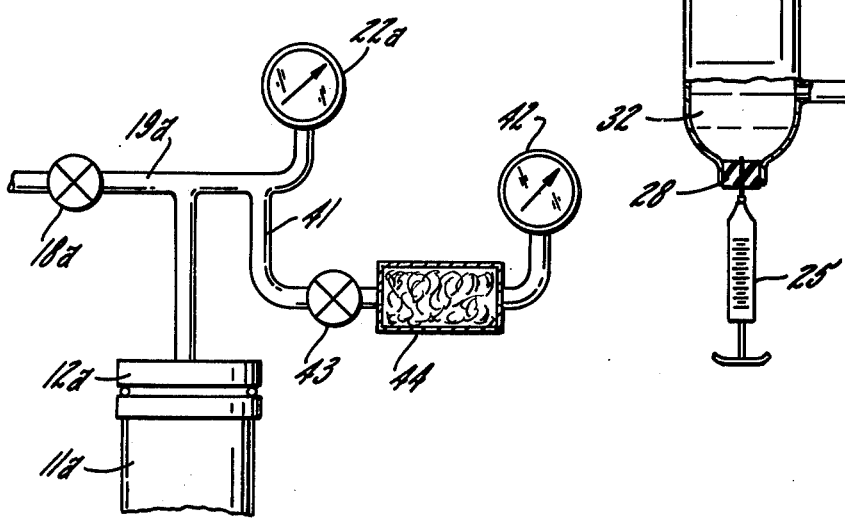
FIG. 3 is a fragmentary schematic of an alternate embodiment combining the functions of the FIG. 1 apparatus and the FIG. 2 device.

An alternate embodiment is shown in FIG. 3 wherein parts previously described have been given the same reference numerals with the distinguishing suffix $a$ added. In this embodiment, a vessel 11a having a closure 12a is connected by a conduit 19a through a valve 18a to a pump, not shown, and through a line 24a to a guage 22a. The line 24a also opens to a line 41 connected to a second Burdon tube pressure gauge 42 through a $CO_2$ absorber 44 and a valve 43.

In operation, when the vessel 11a is being evacuated, the valve 43 is maintained open so that the line 41, absorber 43 and gauge 42 are also evacuated, reducing the pressure readings of both of the gauges 22a and 42 to virtually zero. After evacuation, the valve 43 is closed along with the valve 18a, and the heating and cooling steps are performed. At that stage of the procedure when the ratio of carbon to nitrogen is to be determined, instead of utilizing the syringe 25 and the nitrometer apparatus 26, the valve 43 is opened while carefully observing the gauge 22a and gas is admitted through the absorber 44 to the gauge 42 until the pressure on the gauge 22a drops a predetermined amount, for example, 10 psi. This has the effect of withdrawing from the now gassified sample a fixed aliquot of gas, of which the $CO_2$ component is absorbed in the absorber 44 and the nitrogen component develops a measurable pressure observable on the gauge 42. By previously empirically calibrating the gauge 42, and its auxiliaries closed off by the valve 43, the pressure on the gauge 42 will conveniently indicate the volume of the non-absorbed gas which is presumably $N_2$, and the calculations referred to above can be completed.

In an illustrative embodiment of the invention, a stainless steel vessel 11, ½ inch I.D. and ⅝ inches O.D. by 24 inches long is provided with a pressure-tight fitting 12 and with conduits as described previously leading to a vacuum pump 20 and a pressure gauge 22. Typically, 0.5 grams of finely comminuted sample, e.g., feed grain, is mixed with 10 grams of cupric oxide to constitute the initial sample 15, and 5 grams of additional cupric oxide is placed atop the sample as the layer 16. The sample is then evacuated to < 1 m.m. mercury pressure absolute, whereupon the valve 18 is closed off and the vessel 11 contents heated to approximately 650° C, over 5 minutes and maintained at about that temperature for an additional 5 minutes.

After withdrawal of the vessel 11 from the heater 21, the vessel is rapidly cooled by placement in a water bath, and a pressure of 90 p.s.i.a. is read from the gauge 22.

A 50 cc. sample is withdrawn from the syringe 25 and transferred to the nitrometer apparatus 26 for $CO_2$ absorption. The nitrometer apparatus indicates 10 cc's of non-absorbed gas, presumed to be nitrogen.

The volumetric ratio of absorbed gas ($CO_2$) to non-absorbed gas ($N_2$) is 10/50. This is ½ the elemental ratio of carbon to nitrogen in the original sample, for an atomic ratio of 2.5.

The internal volume of vessel 11 plus the volume of the tube 24 and gauge 22 must be determined accurately, and in a typical apparatus, this volume amounts to 80 cc.

Then at 90 lb. absolute gauge pressure, at sea level, the apparatus will contain 0.0219 moles of gas. Thus the initial sample is composed of 35% carbon and 24.5% nitrogen. The remainder of the sample is presumed to be made up of hydrogen, oxygen and perhaps other elements, none of which affect the analysis for carbon and nitrogen.

I claim as my invention:

1. An analytical method for determining the elemental carbon and nitrogen contents of a sample, which comprises:
   mixing a predetermined amount of said sample, in finely divided form, with an excess of a cupric oxide oxidizing agent,
   evacuating a pressure vessel containing said mixture,
   heating said mixture to a temperature sufficient to effect oxidation of said sample and thereby convert carbon to $CO_2$, nitrogen to $N_2$, and hydrogen to water,
   cooling said vessel to condense water,
   determining the resulting gas pressure as a measure of the total carbon plus nitrogen content of the original sample,
   withdrawing a predetermined volume of said gas,
   sorbing $CO_2$ from said predetermined volume of gas,
   and determining the change in volume of said gas as a measure of the ratio of carbon to nitrogen in the original sample.

2. The method of claim 1 wherein said predetermined volume is withdrawn by a hypodermic syringe.

3. The method of claim 1 wherein said sorbing of the $CO_2$ and said measuring the change in volume of said gas are effected by the nitrometer technique with an alkaline reagent.

4. The method of claim 1 wherein said predetermined volume is withdrawn by an evacuated $CO_2$ absorber and associated pressure gauge.

* * * * *